United States Patent
Sims et al.

(10) Patent No.: US 9,039,732 B2
(45) Date of Patent: May 26, 2015

(54) SURGICAL FORCEPS

(75) Inventors: Grant T. Sims, Littleton, CO (US);
Chase Collings, Hayden, ID (US);
Jeffrey R. Townsend, Loveland, CO (US)

(73) Assignee: Covidien LP, Mansfield, MA (US)

( * ) Notice: Subject to any disclaimer, the term of this patent is extended or adjusted under 35 U.S.C. 154(b) by 962 days.

(21) Appl. No.: 13/179,975

(22) Filed: Jul. 11, 2011

(65) Prior Publication Data
US 2013/0018372 A1   Jan. 17, 2013

(51) Int. Cl.
*A61B 18/14* (2006.01)
*A61B 17/285* (2006.01)
*A61B 17/28* (2006.01)
*A61B 18/00* (2006.01)

(52) U.S. Cl.
CPC .......... *A61B 17/285* (2013.01); *Y10T 29/4984* (2015.01); *A61B 18/1442* (2013.01); *A61B 2017/2825* (2013.01); *A61B 2018/1455* (2013.01); *A61B 2018/0063* (2013.01); *A61B 2018/1495* (2013.01)

(58) Field of Classification Search
CPC ................... A61B 18/1442; A61B 2018/0063; A61B 2018/1455; A61B 2018/1495
USPC ...................... 606/51, 52, 205, 207
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,219,354 A | 6/1993 | Choudhury et al. |
| D343,453 S | 1/1994 | Noda |
| D348,930 S | 7/1994 | Olson |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

International Search Report corresponding application PCT/US2012/046085 mailed Jan. 31, 2013.

(Continued)

*Primary Examiner* — Joseph Stoklosa
*Assistant Examiner* — Jocelyn D Ram

(57) ABSTRACT

A forceps includes first and second shaft members each having a jaw member disposed at a distal end thereof. One (or both) of the first and second jaw members is moveable relative to the other between a spaced-apart position and an approximated position for grasping tissue therebetween. The first jaw member includes a jaw frame fixedly engaged to the first shaft member and a disposable jaw housing releasably engageable with the jaw frame. The disposable jaw housing includes a knife assembly disposed therein. The knife assembly includes a knife blade biased toward an initial position, wherein the knife blade is disposed within the jaw housing. The knife blade is moveable between the initial position and an extended position, wherein the knife blade extends at least partially from the jaw housing to cut tissue grasped between the first and second jaw members.

8 Claims, 9 Drawing Sheets

(56) References Cited

U.S. PATENT DOCUMENTS

| | | | |
|---|---|---|---|
| D349,341 S | 8/1994 | Lichtman et al. | |
| D354,564 S | 1/1995 | Medema | |
| D358,887 S | 5/1995 | Feinberg | |
| 5,599,350 A * | 2/1997 | Schulze et al. | 606/51 |
| D384,413 S | 9/1997 | Zlock et al. | |
| 5,693,051 A * | 12/1997 | Schulze et al. | 606/51 |
| H1745 H | 8/1998 | Paraschac | |
| D402,028 S | 12/1998 | Grimm et al. | |
| 5,876,401 A * | 3/1999 | Schulze et al. | 606/51 |
| D408,018 S | 4/1999 | McNaughton | |
| D416,089 S | 11/1999 | Barton et al. | |
| 6,050,996 A * | 4/2000 | Schmaltz et al. | 606/51 |
| D424,694 S | 5/2000 | Tetzlaff et al. | |
| D425,201 S | 5/2000 | Tetzlaff et al. | |
| H1904 H | 10/2000 | Yates et al. | |
| 6,174,309 B1 * | 1/2001 | Wrublewski et al. | 606/45 |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| 6,464,704 B2 | 10/2002 | Schmaltz et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| 7,033,356 B2 * | 4/2006 | Latterell et al. | 606/48 |
| 7,041,102 B2 * | 5/2006 | Truckai et al. | 606/51 |
| D525,361 S | 7/2006 | Hushka | |
| D531,311 S | 10/2006 | Guerra et al. | |
| 7,118,570 B2 * | 10/2006 | Tetzlaff et al. | 606/48 |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| 7,632,269 B2 * | 12/2009 | Truckai et al. | 606/51 |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 2002/0058965 A1 | 5/2002 | Andrews | |
| 2002/0107517 A1 | 8/2002 | Witt et al. | |
| 2003/0171747 A1 | 9/2003 | Kanehira et al. | |
| 2003/0220637 A1 * | 11/2003 | Truckai et al. | 606/28 |
| 2005/0159745 A1 * | 7/2005 | Truckai et al. | 606/51 |
| 2006/0079891 A1 | 4/2006 | Arts et al. | |
| 2008/0243106 A1 * | 10/2008 | Coe et al. | 606/1 |
| 2009/0112246 A1 * | 4/2009 | Weisshaupt et al. | 606/174 |
| 2009/0157074 A1 * | 6/2009 | Livneh | 606/37 |
| 2010/0004208 A1 | 1/2010 | Chaplin et al. | |
| 2010/0228250 A1 * | 9/2010 | Brogna | 606/45 |
| 2010/0292691 A1 * | 11/2010 | Brogna | 606/45 |
| 2011/0004208 A1 * | 1/2011 | Truckai et al. | 606/45 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 133991 A2 | 3/1985 |
| EP | 1159926 | 12/2001 |
| EP | 1330991 A1 | 7/2003 |
| EP | 1645658 A1 | 4/2006 |
| JP | 61-501068 | 9/1984 |
| JP | 6-502328 | 3/1992 |
| JP | 5-5106 | 1/1993 |
| JP | 5-40112 | 2/1993 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2004-517668 | 6/2004 |
| JP | 2004-528869 | 9/2004 |
| SU | 401367 | 11/1974 |
| WO | WO 00/36986 | 6/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 2000, Thomas P. Ryan.
U.S. Appl. No. 12/336,970, filed Dec. 17, 2008, Paul R. Sremeich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.

(56) References Cited

OTHER PUBLICATIONS

U.S. Appl. No. 12/759,551, filed Apr. 13, 2010, Glenn A. Horner.
U.S. Appl. No. 12/769,444, filed Apr. 28, 2010, Glenn A. Norner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, Vol. 1, nr. 5431 p. 361, ISSN: 0007-1447.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.

(56) References Cited

OTHER PUBLICATIONS

Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.

(56) References Cited

OTHER PUBLICATIONS

Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Supplementary European Search Report from corresponding application EP 12 81 2005 dated Dec. 19, 2014.

* cited by examiner

SURGICAL FORCEPS

BACKGROUND

The present disclosure relates to a surgical forceps and, more particularly, to a surgical forceps including replaceable jaw members.

TECHNICAL FIELD

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member which effectively severs the tissue after forming a tissue seal.

Generally, surgical instruments, including forceps, can be classified as single-use instruments, e.g., instruments that are discarded after a single use, partially-reusable instruments, e.g., instruments including both disposable portions and portions that are sterilizable for reuse, and completely reusable instruments, e.g., instruments that are completely sterilizable for repeated use. As can be appreciated, those instruments (or components of instruments) that can be sterilized and reused help reduce the costs associated with the particular surgical procedure for which they are used. However, although reusable surgical instruments are cost-effective, it is important that these instruments be capable of performing the same functions as their disposable counterparts and that any disposable components of these instruments be efficiently removable and replaceable with new components.

SUMMARY

In accordance with one embodiment of the present disclosure, a forceps is provided. The forceps includes first and second shaft members. Each shaft member has a jaw member disposed at a distal end thereof. One (or both) of the first and second jaw members is moveable relative to the other between a spaced-apart position and an approximated position for grasping tissue therebetween. The first jaw member includes a jaw frame fixedly engaged to the first shaft member. The first jaw member further includes a disposable jaw housing releasably engageable with the jaw frame. The disposable jaw housing includes a knife assembly disposed therein. The knife assembly includes a knife blade biased toward an initial position and moveable between the initial position and an extended position. In the initial position, the knife blade is disposed within the jaw housing. In the extended position, the knife blade extends partially (or entirely) from the jaw housing, e.g., for cutting tissue grasped between the first and second jaw members.

In one embodiment, the forceps further includes an actuator disposed within the jaw frame. The actuator is selectively moveable from an un-actuated position to an actuated position to move the knife blade from the initial position to the extended position.

In another embodiment, the forceps includes a third shaft member. The third shaft member is coupled to the actuator and extends proximally therefrom. The third shaft member is moveable between a first position and a second position to move the actuator between the un-actuated position and the actuated position.

In yet another embodiment, the jaw housing is formed partially (or entirely) from an electrically-insulative material.

In still another embodiment, the forceps further includes a seal plate engaged to the jaw housing. The seal plate includes a longitudinally-extending blade channel defined therein. The blade channel is configured to permit passage of the knife blade therethrough upon movement of the knife blade from the initial position to the extended position. Further, the seal plate may be adapted to connect to a source of electrosurgical energy for conducting energy through tissue grasped between the first and second jaw members.

In still yet another embodiment, the second jaw member includes a jaw frame fixedly engaged to the second shaft member and a disposable jaw housing releasably engageable with the jaw frame. Similar to the first jaw member, the second jaw member may further include a seal plate engaged to the jaw housing.

In another embodiment, the seal plate of the second jaw member includes a longitudinally-extending blade channel defined therethrough. The blade channel of the second jaw member is configured for passage of the knife blade therethrough upon movement of the knife blade to the extended position.

In yet another embodiment, the jaw housing(s) includes one or more engagement features configured to releasably engage complementary engagement features defined within the jaw frame, e.g., for releasably engaging the jaw housing(s) to the respective jaw frame(s).

In still another embodiment, the first and second shaft members and the jaw frame are sterilizable. The third shaft member may also be sterilizable, while the remaining components may be discarded after a single use.

In still yet another embodiment, the knife assembly includes a resiliently flexible member disposed within the jaw housing. The resiliently flexible member engages the knife blade thereon and biases the knife blade toward the initial position. Further, the resiliently flexible member may be formed partially (or entirely) from silicon.

A disposable jaw member configured for releasably engaging an end effector assembly of a forceps is provided in accordance with another embodiment of the present disclosure. The disposable jaw member includes a jaw housing that is releasably engageable with a jaw frame of the end effector assembly. A seal plate is engaged to the jaw housing and includes a longitudinally-extending blade channel defined therethrough. A knife assembly is coupled to the jaw housing and is disposed between the jaw housing and the seal plate. The knife assembly including a longitudinally-extending knife blade coupled thereto and moveable between an initial position and an extended position. The knife blade is biased toward the initial position, wherein the knife blade is disposed within the jaw housing. In the extended position, the knife blade extends through the blade channel of the seal plate.

In one embodiment, the knife assembly includes a resiliently flexible member disposed within the jaw housing. The resiliently flexible member engages the knife blade thereon and biases the knife blade toward the initial position. Similar to the previous embodiment, the resiliently flexible member may be formed partially (or entirely) from silicon.

In another embodiment, the jaw housing is formed at least partially from an electrically-insulative material. Further, the seal plate may be adapted to connect to a source of electrosurgical energy for conducting energy through tissue.

In still another embodiment, the forceps includes an actuator disposed within the jaw frame. The actuator is selectively moveable from an un-actuated position to an actuated position to move the knife blade from the initial position to the extended position.

In yet another embodiment, the jaw housing includes one or more engagement features configured to releasably engage complementary engagement feature(s) defined within the jaw frame.

A method of assembling a jaw member, e.g., any of the jaw members discussed above, is also provided in accordance with the present disclosure. The method includes providing a jaw housing, a seal plate having a longitudinally-extending blade channel defined therethrough, and a knife assembly having a longitudinally-extending knife blade coupled thereto. First, the seal plate is positioned on the knife assembly such that the blade channel of the seal plate and the knife blade are aligned in vertical registration with one another. The jaw housing is then slidably positioned about the knife assembly and the seal plate such that the jaw housing, the seal plate, and the knife assembly are retained in fixed relation relative to one another.

In one embodiment, the method further includes providing a jaw frame including an actuator disposed therein. The jaw housing is releasably engaged to the jaw frame such that the blade channel of the seal plate, the knife blade of the knife assembly, and the actuator of the jaw frame are aligned in vertical registration with one another.

In another embodiment, the knife assembly is formed from a resiliently compressible material. The knife assembly is configured to be compressed from an initial state to a compressed state upon positioning of the jaw housing about the seal plate and the knife assembly such that a bias of the insulator back toward the initial state frictionally retains the jaw housing, the seal plate, and the knife assembly in fixed relation relative to one another.

BRIEF DESCRIPTION OF THE DRAWINGS

Various embodiments of the subject instrument are described herein with reference to the drawings wherein.

DETAILED DESCRIPTION

Figure 1:
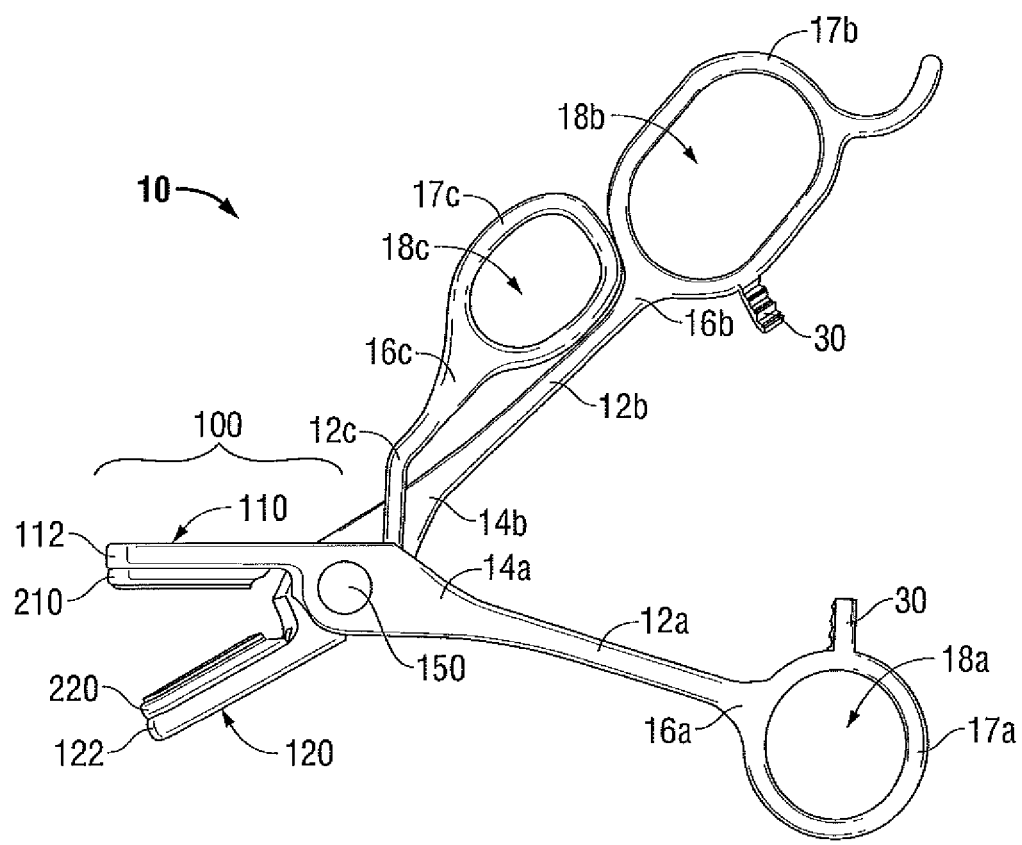
FIG. 1 is a side, perspective view of one embodiment of a forceps provided in accordance with the present disclosure wherein jaw members of the forceps are shown in a spaced-apart position.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 2:
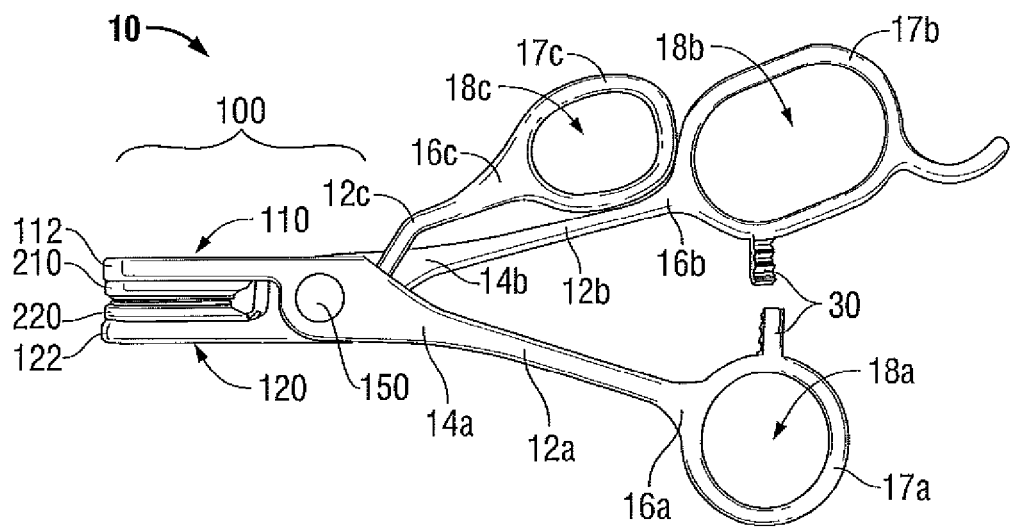
FIG. 2 is a side, perspective view of the forceps of FIG. 1 wherein the jaw members are shown in an approximated position.

Referring initially to FIGS. 1 and 2, a forceps 10 is shown including two elongated shafts 12a and 12b each having a distal end 14a and 14b and a proximal end 16a and 16b, respectively. An end effector assembly 100 including opposing jaw members 110, 120, is attached to distal ends 14a and 14b of shafts 12a and 12b, respectively. Opposing jaw members 110 and 120 are pivotably connected about a pivot pin 150 and are moveable relative to one another between a spaced-apart position (FIG. 1) and an approximated position (FIG. 2) for grasping tissue therebetween. Further, each jaw member 110, 120 includes a disposable component 210, 220, respectively, that is releasably engaged thereon. Although forceps 10 is shown as an open surgical forceps, jaw members 110, 120 including disposable components 210, 220, respectively, may similarly be configured for use with an endoscopic surgical forceps (not shown).

With continued reference to FIGS. 1 and 2, each shaft 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of shafts 12a and 12b relative to one another that, in turn, pivots jaw members 110 and 120 between the spaced-apart position (FIG. 1) and the approximated position (FIG. 2), wherein the jaw members 110 and 120 cooperate to grasp tissue therebetween.

A ratchet 30 may be included for selectively locking jaw members 110, 120 relative to one another at various positions during pivoting. The ratchet 30 may include graduations or other visual markings that enable the user to easily and quickly ascertain and control the amount of closure force between the jaw members 110 and 120.

Figure 3:
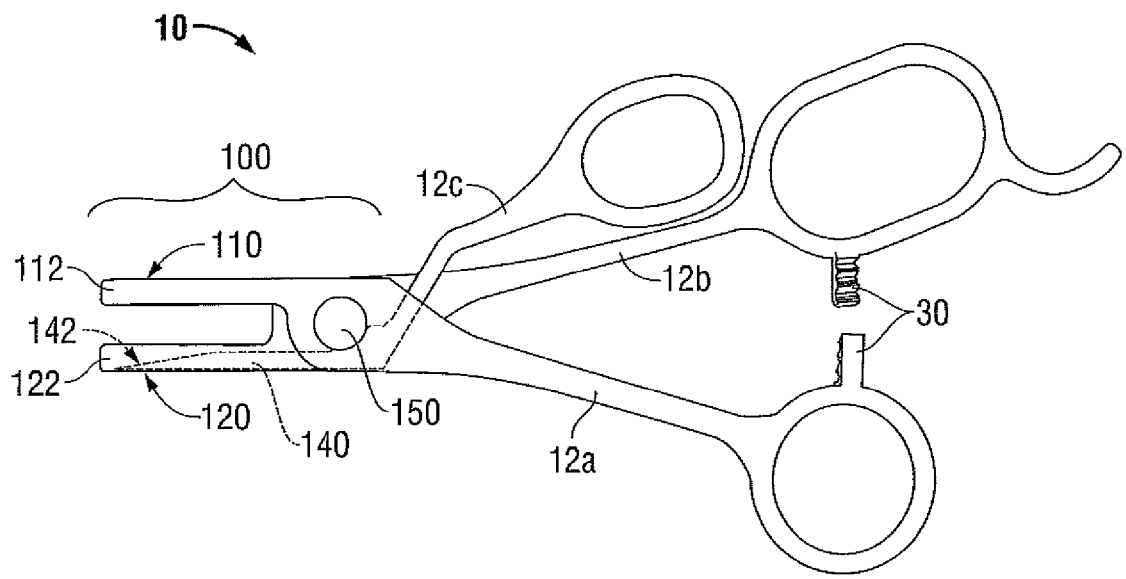
FIG. 3 is a side, perspective, transparent view of the forceps of FIG. 1, wherein an actuator is shown in an un-actuated position.
Figure 4:
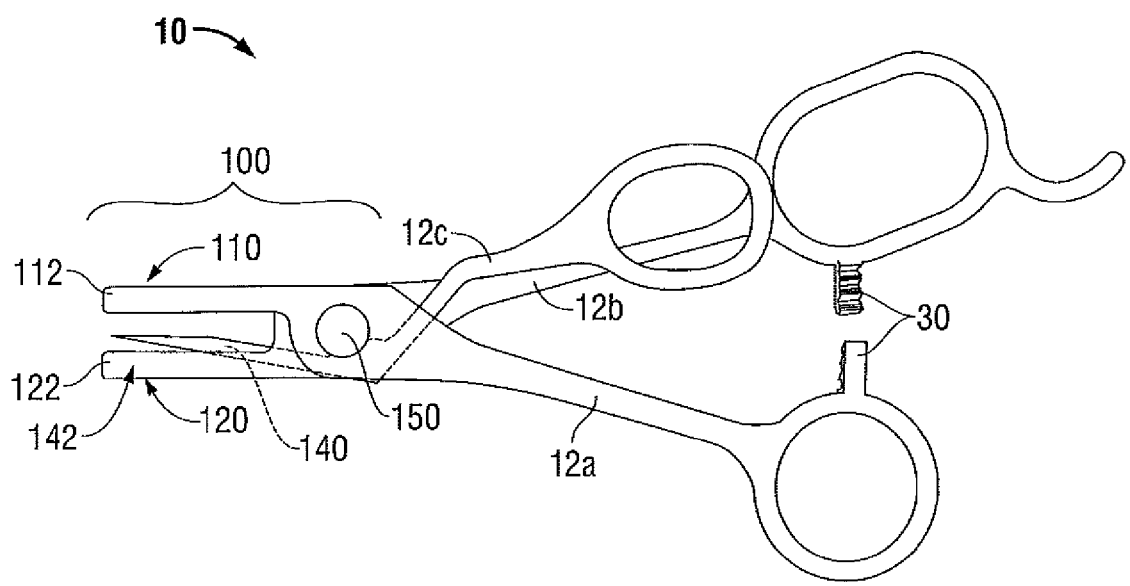
FIG. 4 is a side, perspective, transparent view of the forceps of FIG. 1, wherein the actuator is shown in an actuated position.

Turning now to FIGS. 3-4, in conjunction with FIGS. 1 and 2, forceps 10 further includes a third shaft 12c extending proximally from an actuator 140 disposed within an actuator slot 142 defined within one of the jaw members, e.g. jaw member 120. Similar to shafts 12a and 12b, third shaft 12c includes a handle 17c disposed at a proximal end 16c thereof. Handle 17c defines a finger hole 18c therethrough that is configured to receive a finger of the user to facilitate movement of shaft 12c between a first position (FIG. 3) and a second position (FIG. 4), wherein actuator 140 extends at least partially from actuator slot 142 defined within jaw member 120. As shaft 12c is moved from the first position to the second position, actuator 140 is moved relative to jaw member 120 from an un-actuated position (FIG. 3) to an actuated position (FIG. 4). As will be described in greater detail below, upon activation of actuator 140, knife blade 261 of knife assembly 260 of disposable component 220 of jaw member 120 (see FIGS. 6A-6F) is urged upwardly between jaw members 110, 120 to cut tissue grasped therebetween.

As best shown in FIGS. 1 and 2, and as mentioned above, forceps 10 includes a pair of jaw members 110, 120. Jaw members 110, 120 each include a disposable component 210, 220 that is releasably engageable with a jaw frame 112, 122, respectively. Jaw frames 112, 122 of jaw members 110, 120, respectively, are fixedly engaged to the respective shafts 12a, 12b, e.g., each jaw frame 112, 122 is formed as a single component with the respective shaft 12a, 12b. Disposable components 210, 220, are removeable from jaw frames 112, 122, respectively, and are replaceable with new disposable components 210, 220, e.g., disposable components are configured to be discarded and replaced after a single use (or a single procedure), while the remaining components of forceps 10, e.g., jaw frames 112, 122, shafts 12a, 12b, 12c, actuator 140, and pivot pin 150, are formed from a sterilizable material, e.g., stainless steel, such that they may be sterilized, e.g., placed in an autoclave, after each procedure for repeated use. As can be appreciated, requiring only a new set of disposable components 210, 220, rather than an entire new surgical instrument, helps reduce the equipment costs associated with performing a particular surgical procedure.

Figure 5A:
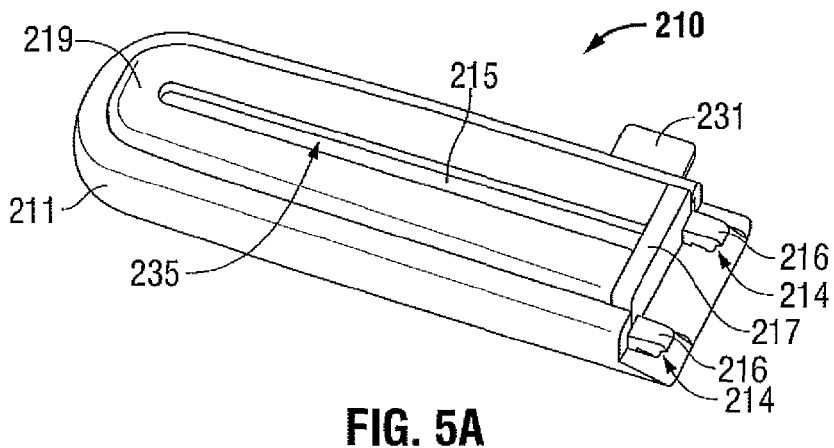
FIG. 5A is a top, perspective view of a disposable portion of one of the jaw members of the forceps of FIG. 1.
Figure 5B:
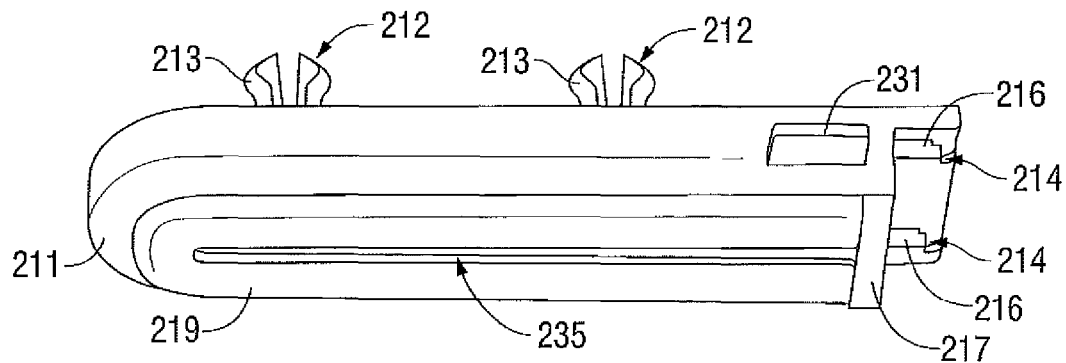
FIG. 5B is an inverted, perspective view of the disposable portion of the jaw member of FIG. 5A.
Figure 5C:
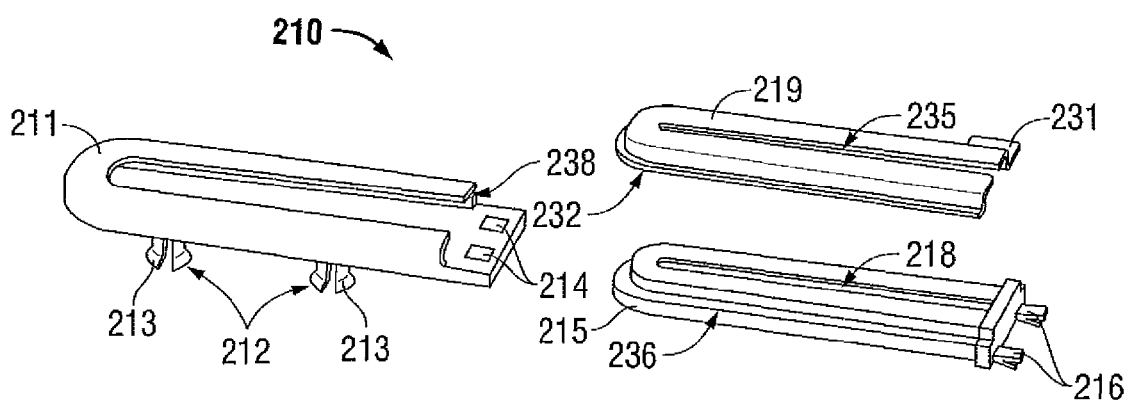
FIG. 5C is an exploded, perspective view of the disposable portion of the jaw member of FIG. 5A.

With reference now to FIGS. 5A-5C, disposable component 210 of jaw member 110 will be described. Disposable component 210 generally includes an insulative jaw housing 211, an insulator 215, and an electrically-conductive tissue sealing plate 219. Jaw housing 211 is configured to mechanically engage insulator 215 and tissue sealing plate 219, e.g., in slidable snap-fit engagement therewith, although other mechanisms (not shown) for releasably securing jaw housing 211 about insulator 215 and tissue sealing plate 219 may be provided. Jaw housing 211 further includes one or more engagement features, e.g., flexible, snap-fit protrusions 212, configured to releasably engage jaw housing 211 to jaw frame 112 of jaw member 110 (see FIG. 7). More specifically, flexible, snap-fit protrusions 212 of jaw housing 211 are configured for insertion through complementary-shaped apertures 113 defined within jaw frame 112 (see FIG. 7) such that jaw housing 211 may be releasably secured to jaw frame 112. Further, protrusions 212 disposed on jaw housing 211 may be longitudinally and laterally offset relative to one another such that tilting, rotating, or other movement of disposable component 210 relative to jaw frame 112 is substantially inhibited once disposable component 210 is engaged to jaw frame 112.

Figure 7:
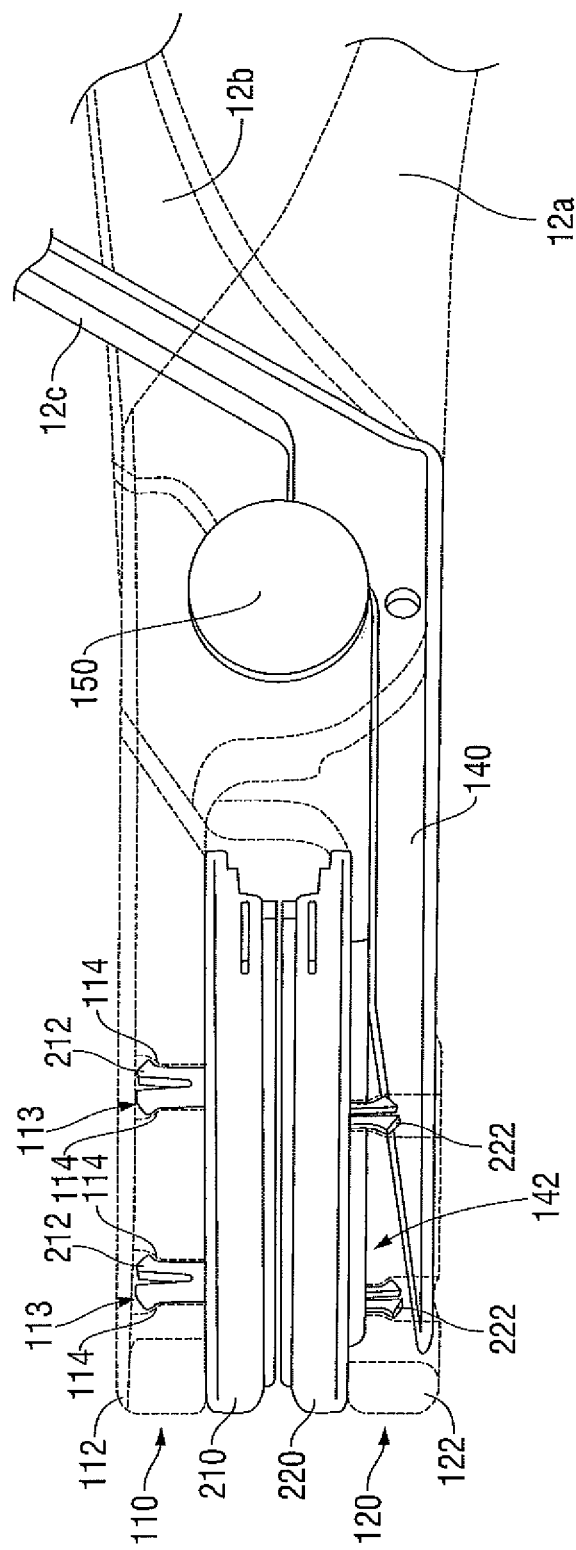
FIG. 7 is an enlarged, perspective view of an end effector assembly of the forceps of FIG. 1 including the disposable portions of FIGS. 5A and 6A engaged thereto.

During assembly, as best shown in FIG. 7, flexible, snap-fit protrusions 212 of jaw housing 211 are aligned with apertures 113 of jaw frame 112. Next, jaw housing 211 and jaw frame 112 are approximated relative to one another until tabs 213 disposed on the free ends of flexible, snap-fit protrusions 212 of jaw housing 211 snap into engagement with notches 114 defined within the interior surfaces of apertures 113 of jaw frame 112. An audible and/or tactile "snap," or other feedback signal, may be provided to alert the user that jaw housing 211 has been securely engaged within jaw frame 112.

In order to disengage jaw housing 211 from jaw frame 112, jaw housing 211 and jaw frame 112 are pulled apart from one another with sufficient force such that tabs 213 of flexible snap-fit protrusions 212 of jaw housing 211 are disengaged from notches 114 of apertures 113 of jaw frame 112, allowing jaw housing 211 to be removed from jaw frame 112. Similarly as described above, an audible and/or tactile "snap," or other feedback signal, may alert the user that jaw housing 211 has been disengaged from jaw frame 112.

Continuing with reference to FIGS. 5A-5C, insulator 215 is formed at least partially from an electrically-insulative material and is configured to electrically isolate tissue sealing plate 219 from the remaining components of jaw member 110. Insulator 215 is slidably disposable within jaw housing 211 and is configured to mechanically engage tissue sealing plate 219 thereon. Further, insulator 215 may include one or more proximally-extending flanges 216 configured to engage corresponding slots 214 defined within jaw housing 211 to securely engage tissue sealing plate 219 and insulator 215 within jaw housing 211, once insulator 215 and tissue sealing plate 219 have been slidably positioned within jaw housing 211. Proximal base 217 of insulator 215 is configured to abut the proximal end of tissue sealing plate 219 to retain tissue sealing plate 219 in position within jaw housing 211 once flanges 216 of insulator 215 have been engaged within slots 214 defined within jaw housing 211. Additionally, insulator 215 may be formed at least partially from a compressible material, e.g., silicon, that is compressed, e.g., from an initial state to a compressed state, upon insertion of insulator 215 into jaw housing 211 such that insulator 215 and tissue sealing plate 219 are also frictionally retained within jaw housing 211, e.g., under the biasing force of insulator 215 urging insulator 215 back toward the initial state.

Electrically-conductive tissue sealing plate 219, as mentioned above, is disposed about insulator 215. Tissue sealing plate 219 includes a lateral flange 231 extending therefrom that is configured to electrically connect tissue sealing plate 219 to a source of electrosurgical energy such as an electrosurgical generator (not shown), e.g., via an electrosurgical cable (not shown). As will be described in greater detail below, disposable component 220 of jaw member 120 may similarly include an electrically-conductive tissue sealing plate 229 (see FIGS. 6A-6F) such that electrosurgical energy may be selectively supplied to either or both of the electrically conductive tissue sealing plates 219, 229 of disposable components 210, 220 of jaw members 110, 120, respectively, to seal tissue grasped between jaw members 110 and 120. Further, either (or both) of tissue sealing plates 219, 229 may include lateral flanges 231, 233, respectively, configured to connect tissue sealing plates 219, 229 to a source of energy to supply energy thereto. Alternatively, other suitable mechanisms (not shown) for electrically coupling tissue sealing plates 219, 229 to a source of energy may be provided.

With continued reference to FIGS. 5A-5C, tissue sealing plate 219 of disposable component 210 of jaw member 110 may include a longitudinally-extending blade channel 235 defined therein. Blade channel 235 is configured to permit passage of a knife blade, e.g., knife blade 261 of knife assembly 260 (see FIGS. 6E and 6F), therethrough upon movement of knife blade 261 to the extended position (see FIG. 9). Blade channel 235 may further be configured to facilitate and/or enhance cutting of tissue upon extension of knife blade 261 therethrough. Insulator 215 may similarly include a blade channel 218 defined therein and extending longitudinally therethrough. Blade channel 218 of insulator 215 permits further extension of knife blade 261 (FIGS. 6E and 6F) toward the extended position, as will be described in greater detail below.

Continuing with reference to FIGS. 5A-5C, disposable component 210 of jaw member 110 may come preassembled, e.g., jaw housing 211, insulator 215 and tissue sealing plate 219 may be engaged to one another during manufacturing, or may be configured to be assembled by the user. In either embodiment, disposable component 210 and/or the sub-components thereof (e.g., jaw housing 211, insulator 215 and/or tissue sealing plate 219) may define various configurations such that the user may select a particular disposable component 210 (or sub-component thereof) suitable for the particular surgical procedure to be performed. For example, different disposable components 210 (or the subcomponents thereof) may be configured to define various dimensions, may be formed from various materials, and/or may have various other features to facilitate mechanical, electrical, or frictional tissue dissection and/or tissue sealing of a wide range of tissue sizes and compositions. Further, tissue sealing plate 219 may include blade channel 235 defined therein, or may be configured as a continuous sealing plate 219, e.g., without blade channel 235 defined therein. Other variations are also contemplated. Put more generally, the interchangeability of different disposable components 210 configured for use with forceps 10 permits the user to customize forceps 10 for use in a wide-range of surgical procedures by selecting a particular disposable component 210 (or subcomponent thereof) suitable for the particular surgical procedure. As can be appreciated, such a configuration reduces the overall number of different surgical instruments needed to perform a wide-range of surgical procedures, thereby helping to reduce overall equipment costs, which, in turn, helps reduce the costs associated with a particular surgical procedure.

Figure 6A:
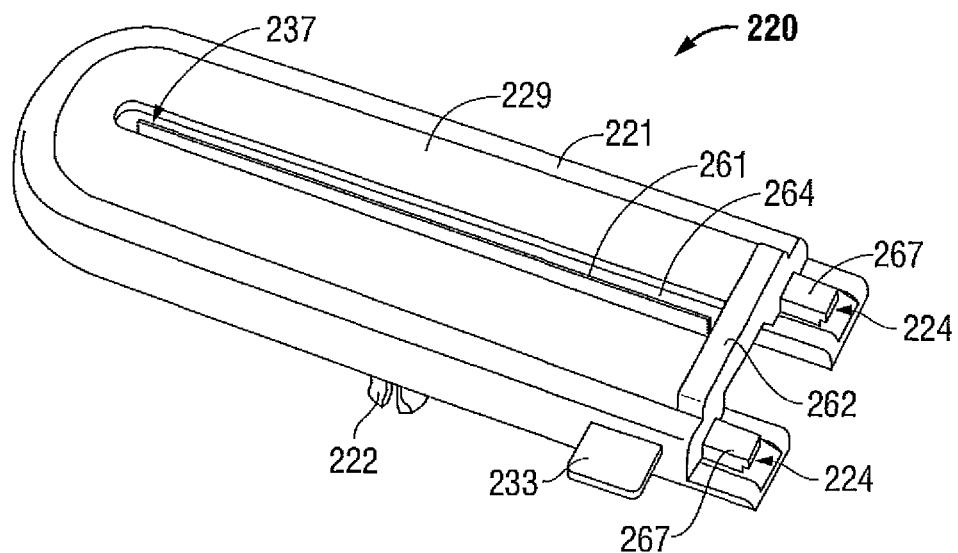
FIG. 6A is a top, perspective view of a disposable portion of the other jaw member of the forceps of FIG. 1.
Figure 6B:
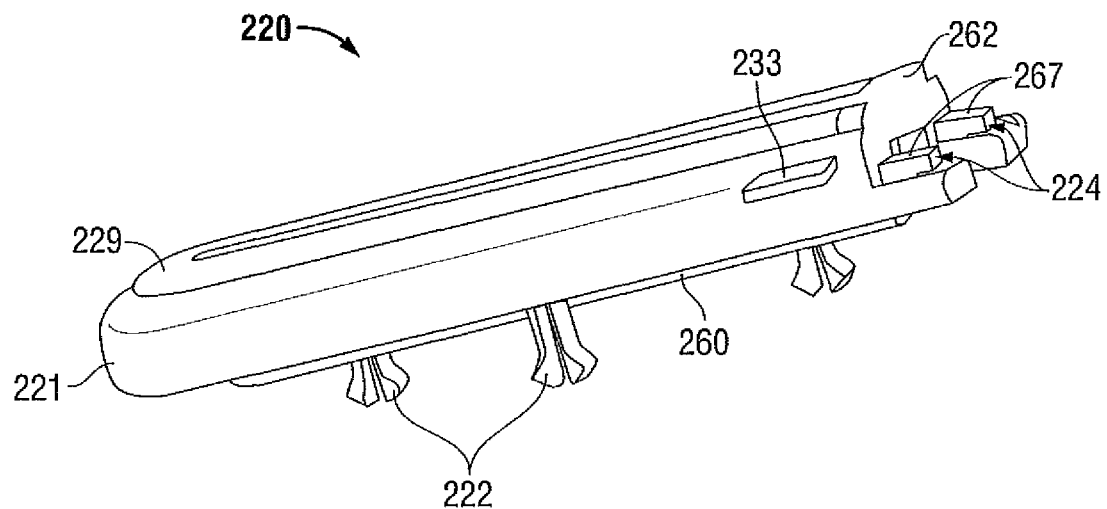
FIG. 6B is a side, perspective view of the disposable portion of the jaw member of FIG. 6A.
Figure 6C:
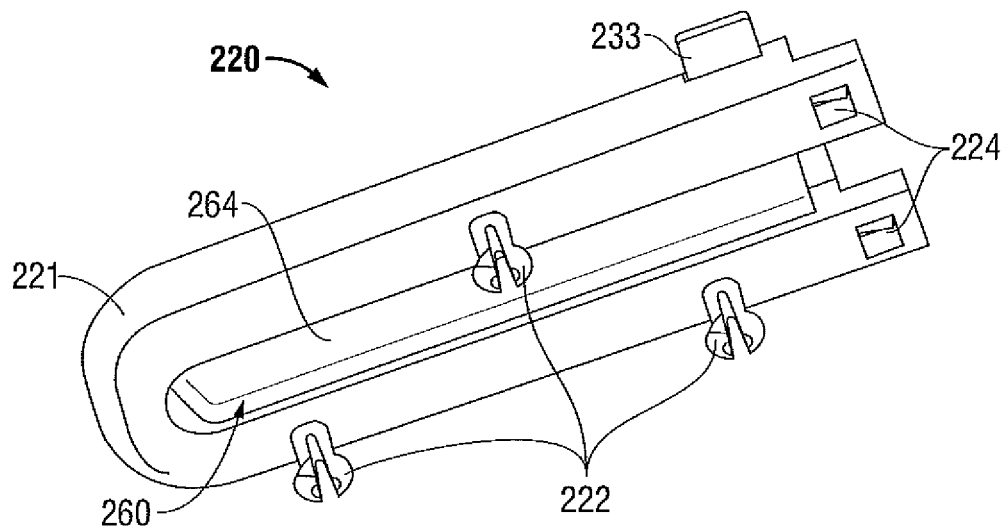
FIG. 6C is a bottom, perspective view of the disposable portion of the jaw member of FIG. 6A.
Figure 6D:
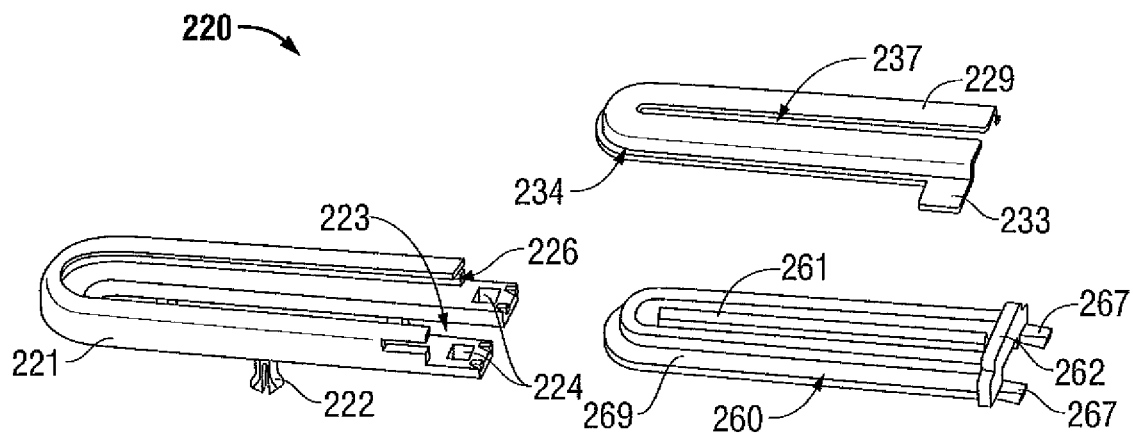
FIG. 6D is an exploded, perspective view of the disposable portion of the jaw member of FIG. 6A.
Figure 6E:
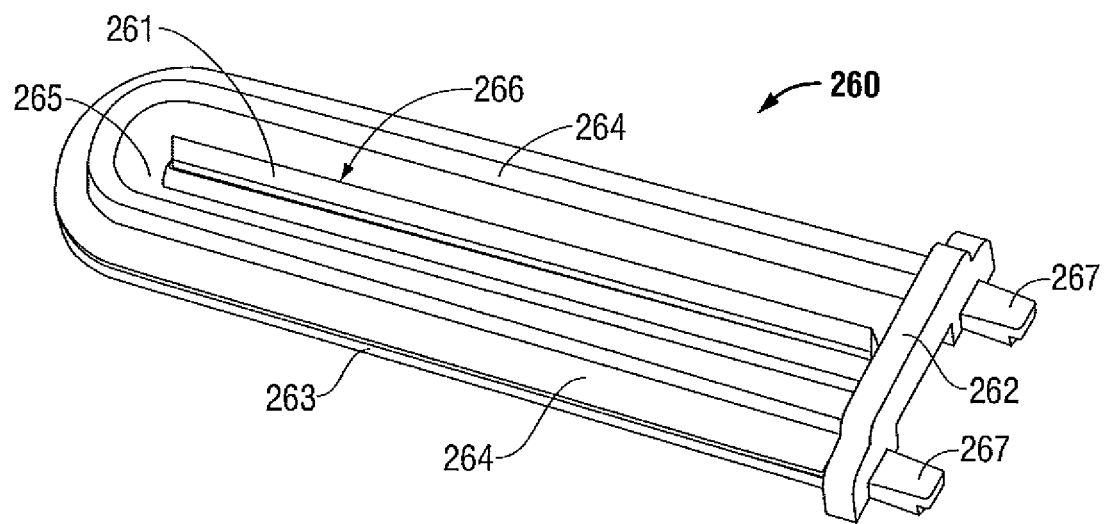
FIG. 6E is a top, perspective view of a knife assembly of the disposable portion of the jaw member of FIG. 6A.
Figure 6F:
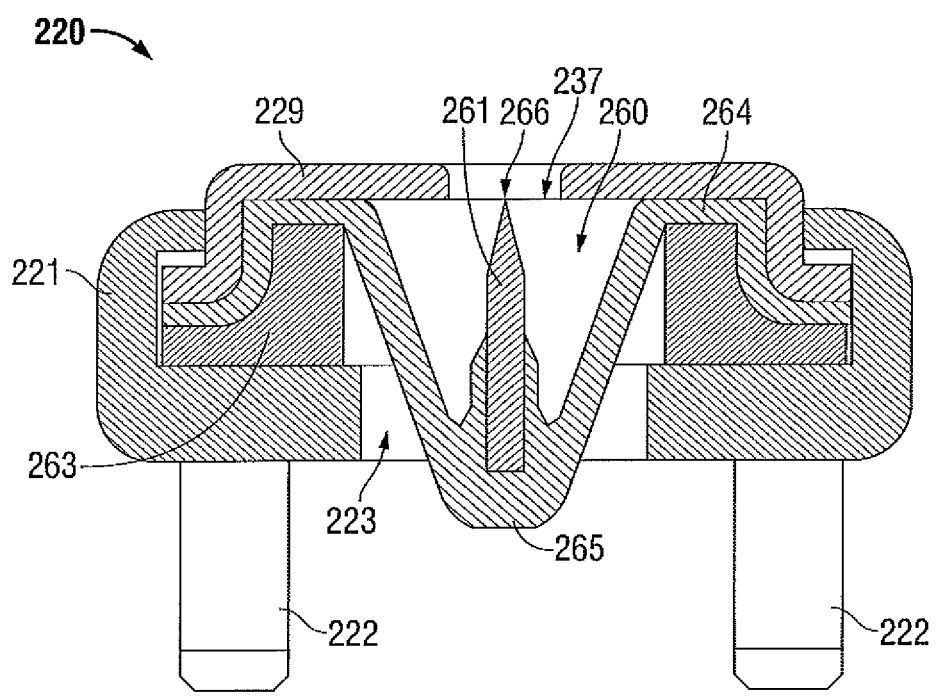
FIG. 6F is a transverse, cross-sectional view of the disposable portion of the jaw member of FIG. 6A.

Turning now to FIGS. 6A-6F, disposable component 220 of jaw member 120 will be described. Disposable component 220 of jaw member 120 includes an insulative jaw housing 221, a knife assembly 260, and a tissue sealing plate 229. Jaw housing 221 is similar to jaw housing 211 of disposable component 210 of jaw member 110 and is configured to mechanically engage knife assembly 260 and tissue sealing plate 229 in slidable snap-fit engagement therewith, although other mechanisms (not shown) are contemplated. Similar to jaw housing 211, jaw housing 221 further includes one or more flexible, snap-fit protrusions 222 configured to releasably engage jaw housing 221 to jaw frame 122 of jaw member 120 (see FIG. 7). An audible and/or tactile "snap," or other feedback signal, may be provided to alert the user as to the engagement (or disengagement) of jaw housing 221 and jaw frame 122. Further, as best shown in FIGS. 6C, 6D and 6F, jaw housing 221 is formed in a horseshoe-shaped or U-shaped configuration to define an elongated aperture 223 therethrough.

Continuing with reference to FIGS. 6A-6F, and in particular to FIGS. 6E and 6F, knife assembly 260 is formed at least partially from an electrically-insulative material and includes a proximal base 262, a horseshoe-shaped frame 263 extending distally from proximal base 262, and a resiliently flexible body 264 engaged to and depending from horseshoe-shaped frame 263. Resiliently flexible body 264 of knife assembly 260 may be formed from an electrically-insulative material that is resiliently flexible. Knife blade 261 is engaged within resiliently flexible body 264, e.g., via injection molding or other suitable engagement, and extends longitudinally therealong. More specifically, resiliently flexible body 264 of knife assembly 260 defines an elongated "V"-shaped configuration that is engaged to horseshoe-shaped frame 263 along an outer periphery thereof and depends therefrom. Knife blade 261 is centered on trough 265 of "V"-shaped body 264 and extends upwardly therefrom to define a cutting edge 266. Resiliently flexible body 264 biases knife blade 261 toward an initial position, as shown in FIG. 7, wherein the trough 265 of resiliently flexible body 264 and knife blade 261 extend downwardly through horseshoe-shaped frame 263 of knife assembly 260 and through elongated aperture 223 defined through horseshoe-shaped jaw housing 221. As will be described in greater detail below, resiliently flexible body 264 and, thus, knife blade 261 are moveable between the initial position and an extended position for cutting tissue grasped between jaw members 110, 120.

With continued reference to FIGS. 6A-6F, tissue sealing plate 229 is positionable about knife assembly 260. More specifically, tissue sealing plate 229 is configured to sit atop resiliently flexible body 264 of knife assembly 260 such that knife blade 261 is aligned with longitudinally-extending blade channel 237 defined through tissue sealing plate 229 and such that the proximal end of tissue sealing plate 229 abuts proximal base 262 of knife assembly 260. As can be appreciated, blade channel 237 is configured to permit extension of knife blade 261 of knife assembly 260 therethrough. Further, blade channel 237 may be configured to facilitate and/or enhance cutting of tissue during extension of knife blade 261 therethrough. As discussed above, tissue sealing plate 229 may include a lateral flange 233 adapted to connect tissue sealing plate 229 to a source of electrosurgical energy for energizing tissue sealing plates 219, 229 of jaw members 110, 120, respectively. Jaw housing 221 and/or tissue sealing plate 229 may otherwise be configured similarly to jaw housing 211 and tissue sealing plate 219, respectively, of disposable component 210 of jaw member 110, discussed above (see FIGS. 5A-5C).

As best shown in FIG. 6D, with tissue sealing plate 229 disposed about knife assembly 260, knife assembly 260 and tissue sealing plate 229 may be sildably positioned within jaw housing 221. Upon slidable positioning of knife assembly 260 and tissue sealing plate 229 within jaw housing 221, proximally-extending flanges 267 of proximal base 262 of knife assembly 260 engage corresponding slots 224 defined within jaw housing 221 to securely engage knife assembly 260 within jaw housing 221, while proximal base 262 of knife assembly 260 abuts the proximal end of tissue sealing plate 229 to retain tissue sealing plate 229 in position within jaw housing 221. Additionally, body portion 264 and/or frame 263 of knife assembly 260 may be formed at least partially from a compressible material that is compressed upon insertion of knife assembly 260 into jaw housing 221 such that knife assembly 260 and tissue sealing plate 229 are also frictionally retained within jaw housing 221. Further, as mentioned above, in the assembled condition, the trough 265 of resiliently flexible body 264 of knife assembly 260 and knife blade 261 of knife assembly 260 are biased, under the bias of resiliently flexible body 264, to extend downwardly at least partially through horseshoe-shaped frame 263 of knife assembly 260 and elongated aperture 223 defined within horseshoe-shaped jaw housing 221, as best shown in FIG. 6F.

Similar to disposable component 210, discussed above, disposable component 220 may come preassembled, e.g., disposable component 220 may be assembled during manufacturing, or may be configured to be assembled by the user. In either embodiment, similarly as discussed above, disposable component 220 and/or the sub-components thereof (e.g., jaw housing 221, knife assembly 260 and/or tissue sealing plate 229) may define various configurations such that the user may select a particular disposable component 220 (or sub-component thereof) suitable for the particular surgical procedure to be performed. In particular, different knife assemblies 260 may be provided such that the user may select a configuration suitable for the particular surgical procedure to be performed. For example, knife blade 261 of knife assembly 260 may include various different cutting features, e.g., a serrated cutting edge, a curvate portion, an electrically energizeable portion, etc., configured to enhance tissue cutting and/or specifically adapted to cut tissue of a particular composition and/or size. As can be appreciated, integrating the knife assembly 260 into the disposable component 220 not only allows the user to select a specifically-configured knife assembly 260 for use in a particular surgical procedure to be performed, but also provides a new, unused knife blade 261 for each procedure.

Turning now to FIGS. 1-4 and 7-9, the use and operation of forceps 10 will be described. Initially, the reusable portion of forceps 10, shown in FIGS. 3-4, is sterilized and/or prepared for use (or reuse). Next, as shown in FIGS. 5A-7, the particular disposable components 210, 220 to be used are selected, assembled, and engaged to the respect jaw frames 112, 122 of jaw members 110, 120.

More particularly, in order to assemble disposable component 210 of jaw member 110, as shown in FIGS. 5A-5C, and as mentioned above, tissue sealing plate 219 is positioned on insulator 215 such that the proximal end of tissue sealing plate 219 abuts proximal base 217 of insulator 215. As best shown in FIG. 5C, insulator 215 and tissue sealing plate 219 define complementary-shaped configurations such that, once tissue sealing plate 219 is positioned about insulator 215, tissue sealing plate 219 and insulator 215 are retained in fixed lateral orientation relative to one another. Further, when tissue sealing plate 219 is disposed about insulator 219, wing 232 of tissue sealing plate 219 is configured to abut outer lip 236 of insulator 215 around the periphery of both tissue sealing plate 219 and insulator 215, as best shown in FIG. 5C.

With tissue sealing plate 219 disposed about insulator 215, as described above, tissue sealing plate 219 and insulator 215 are slidably engaged within jaw housing 211. More particularly, wing 232 of tissue sealing plate 219 and outer lip 236 of insulator 215 are slid distally into engagement with track 238 defined within jaw housing 211 from the proximal end of jaw housing 211 to the distal end of jaw housing 211 until tissue sealing plate 219 and insulator 215 are substantially fully disposed within jaw housing 211 and such that flanges 216 of insulator 215 engage slots 214 of jaw housing 211, thereby securing tissue sealing plate 219, insulator 215, and jaw housing 211 to one another. Further, in this configuration, tissue sealing plate 219 is inhibited from being lifted, or disengaged from jaw housing 211 via the engagement of wing 232 within track 238 of jaw housing 211. In other words, jaw housing 211 secures insulator 215 and tissue sealing plate 219 therein. Additionally, or alternatively, as mentioned above, insulator 215 may be formed from a resiliently compressible material that is compressed, e.g., from an initial state to a compressed state, in order to allow insulator 215 and tissue sealing plate 219 to be slidably inserted into track 238 of jaw housing 211. Accordingly, once insulator 215 and tissue sealing plate 219 are disposed within jaw housing 211, insulator 215, tissue sealing plate 219, and jaw housing 211 are frictionally secured to one another under the bias of insulator 215, e.g., as insulator 215 attempts to resiliently return to the initial, non-compressed state.

Turning now to FIGS. 6A-6F, the assembly of disposable component 220 will be described. Initially, as mentioned above, tissue sealing plate 229 is positioned on flexible body 264 of knife assembly 260 such that knife blade 261 is vertically aligned with longitudinally-extending blade channel 237 defined through tissue sealing plate 229 and such that the proximal end of tissue sealing plate 229 abuts proximal base 262 of knife assembly 260. Next, knife assembly 260 and tissue sealing plate 229 are sildably inserted into jaw housing 221. More specifically, abutting wing 234 of sealing plate 229 and outer lip 269 of knife assembly 260 are slid through track 226 defined within jaw housing 221 until proximally-extending flanges 267 of proximal base 262 of knife assembly 260 engage corresponding slots 224 defined within jaw housing 221 to securely engage knife assembly 260 within jaw housing 221. In the assembled condition, as best shown in FIG. 6F, knife blade 261 of knife assembly 260 is vertically aligned with both elongated aperture 223 of horseshoe-shaped jaw housing 221 and blade channel 237 defined within sealing plate 229. As mentioned above, knife assembly 260 and sealing plate 229 may also be frictionally retained in engagement within jaw housing 221, e.g., in embodiments where body portion 264 and/or frame 263 of knife assembly 260 are formed from a resiliently compressible material that is compressed from an initial state to a compressed state upon insertion of knife assembly 260 into jaw housing 221.

With disposable components 210, 220 of jaw members 110, 120 fully assembled, as described above, disposable components 210, 220 may be snap-fittingly engaged to their respective jaw frames 112, 122, to complete the assembly of forceps 10. Alternatively, jaw housing 211 may be configured for slidable positioning about insulator 215 and tissue sealing plate 219 as well as the jaw frame 112 to secure disposable component 210 to jaw frame 112 (as opposed to the snap-fitting arrangement discussed above). In other words, insulator 215 and tissue seal plate 219 may first be positioned on jaw frame 112, with jaw housing 211 subsequently slide-fit thereabout to secure insulator 215, tissue sealing plate 219, and jaw frame 112 of jaw member 110 to one another. Similarly, jaw housing 221 may be configured for slidable positioning about knife assembly 260, sealing plate 229, and jaw frame 122 to secure the components of jaw member 120 to one another. In either embodiment, disposable component 220 is engaged to jaw frame 122 of jaw member 120 such that knife blade 261, which is vertically aligned with both elongated aperture 223 of horseshoe-shaped jaw housing 221 and blade channel 237 of sealing plate 229, is also aligned with actuator slot 142 and, thus actuator 140.

At this point (or prior to), an electrosurgical energy source (not shown) may be coupled to tissue sealing plate 219 and/or tissue sealing plate 229 of jaw members 110, 120, respectively, e.g., via an electrosurgical cable (not shown) coupled at a first end to the energy source (not shown) and at a second end to lateral flange 231 and/or lateral flange 233 of tissue sealing plates 219, 229, respectively. However, the electrical connection(s) may alternatively be configured to run through either of shafts 12a, 12b, or may otherwise be configured to supply energy to tissue sealing plates 219, 229 via any other suitable mechanism. With disposable components 210, 220 securely engaged to the respective jaw members 110, 120 (and with the electrical connections intact), forceps 10 is ready for use.

With reference now to FIGS. 1 and 2, and initially to FIG. 1, shafts 12a and 12b are moved apart from one another such that jaw members 110, 120, disposed at distal ends 14a, 14b, of shafts 12a and 12b, respectively, are moved to the spaced-apart position. At this point, shaft 12c, which is coupled to actuator 140, is disposed in the first position, such that actuator 140 is disposed in the un-actuated position, e.g., such that actuator 140 is disposed within actuator slot 142 defined within jaw frame 112, as best shown in FIG. 3.

With jaw members 110, 120 disposed in the spaced-apart position, as shown in FIG. 1, forceps 10 may be manipulated into position such that tissue to be grasped, sealed and/or divided is disposed between jaw members 110, 120. Once tissue is positioned as desired, shafts 12a and 12b may be moved toward one another to pivot jaw members 110, 120 about pivot pin 150 toward the approximated position to grasp tissue between tissue sealing plates 219, 229 of disposable components 210, 220, of jaw members 110, 120 respectively, as best shown in FIGS. 2 and 7. Shafts 12a and 12b may be approximated relative to one another to selectively engage ratchet 30 such that the user may control the closure force applied to tissue grasped between jaw members 110, 120. Next, the user may selectively apply electrosurgical energy to electrically-conductive tissue sealing plates 219 and 229 of jaw members 110 and 120, respectively, to seal tissue grasped between jaw members 110, 120.

Figure 8:
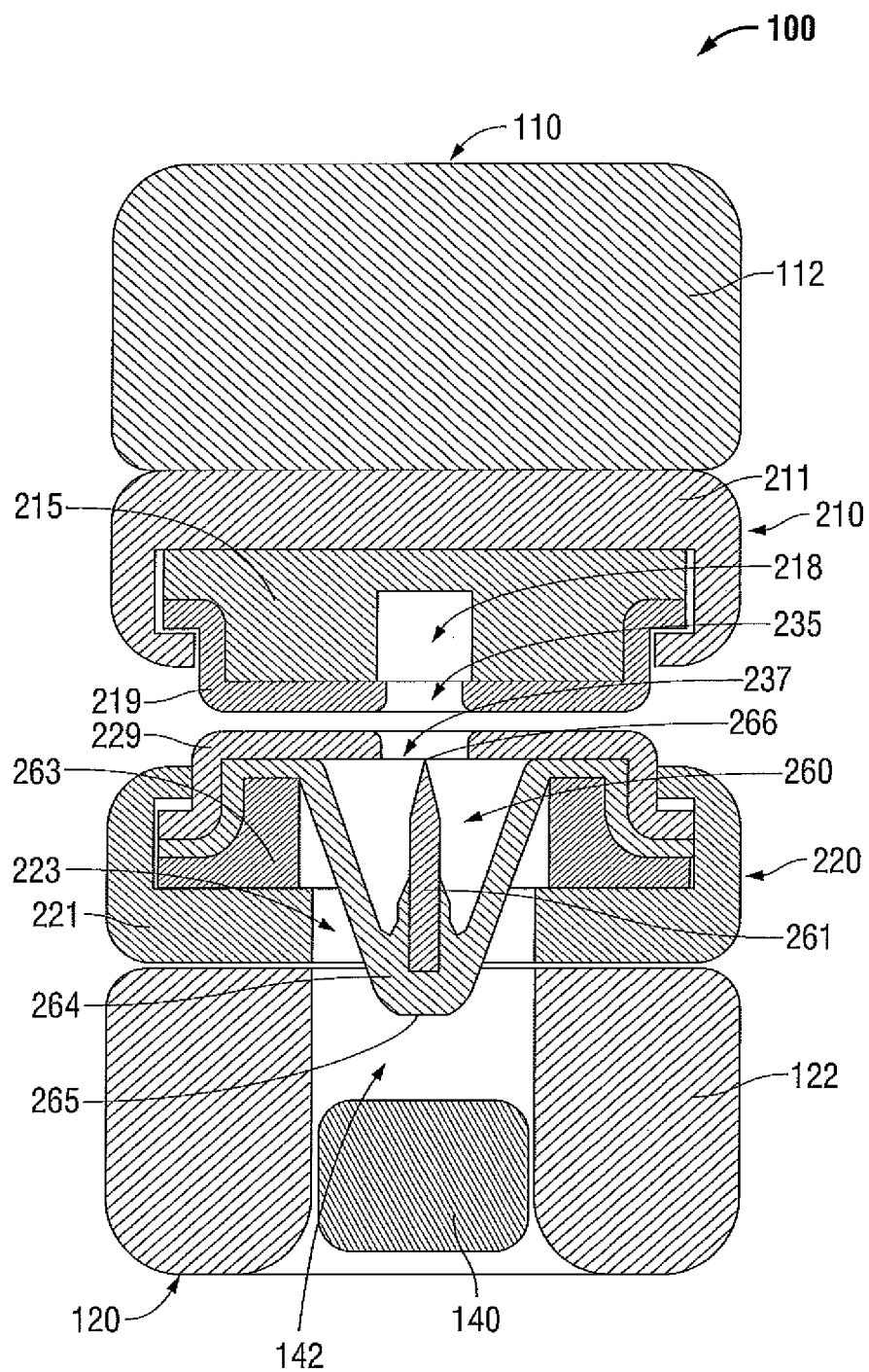
FIG. 8 is a transverse, cross-sectional view of the end effector assembly of FIG. 7, wherein the knife assembly is shown in an initial position.

Once tissue grasped between jaw members 110, 120 has been sealed, or in embodiments where it is only desired to cut tissue, actuator 140 may be activated to advance knife blade 261 to the extended position to cut tissue grasped between jaw members 110, 120. Initially, as shown in FIGS. 7-8, and as mentioned above, actuator 140 is disposed in the un-actuated position, wherein actuator 140 is disposed within actuator slot 142 defined within jaw frame 122. In this position, knife blade 261 of knife assembly 260 remains disposed in the initial position under the bias of resiliently flexible body 264. As such, knife blade 261 remains disposed within jaw housing 221, e.g., knife blade 261 does not extend through blade channel 237 of tissue sealing plate 229.

Figure 9:
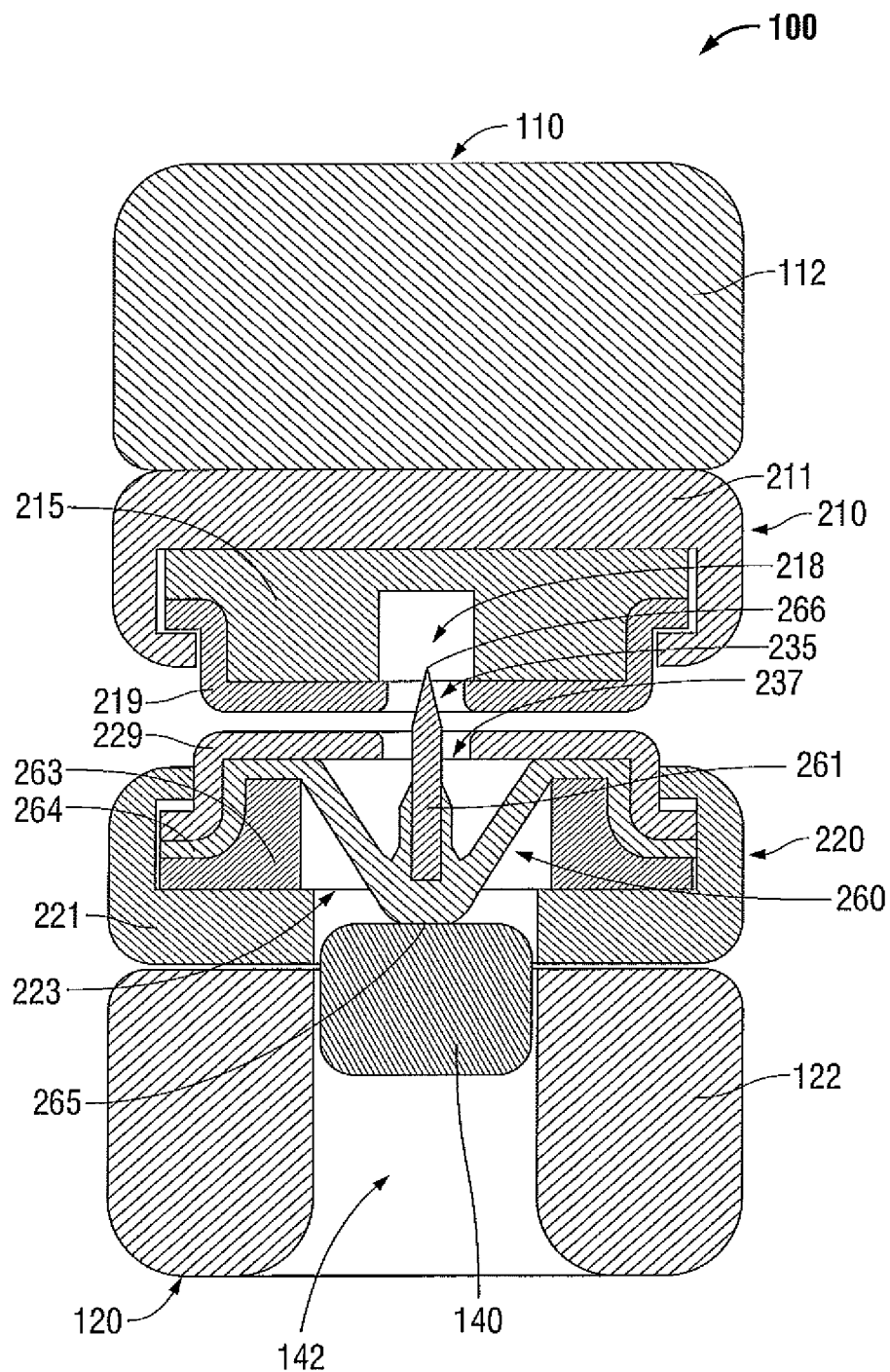
FIG. 9 is a transverse, cross-sectional view of the end effector assembly of FIG. 7, wherein the knife assembly is shown in an extended position.

In order to move knife blade 261 from the initial position to the extended position to cut tissue grasped between jaw members 110, 120, third shaft 12c is moved toward shafts 12a and 12b, e.g., from the first position to a second position. As third shaft 12c is moved relative to shafts 12a and 12b from the first position to the second position, actuator 140 is pivoted about pivot pin 150 and relative to jaw frame 122 of jaw member 120 toward disposable component 220 of jaw member 120, e.g., from the un-actuated position toward the actuated position. As best shown in FIG. 9, upon movement of shaft 12c toward the second position, actuator 140 extends from actuator slot 142 defined within jaw frame 122, eventually contacting resiliently flexible body 264 of knife assembly 260 of disposable component 220 of jaw member 120. More specifically, actuator 140 contacts resiliently flexible body 264 of knife assembly 260 directly below knife blade 261, e.g., at the trough 265 of "V"-shaped resiliently flexible body 264.

With continued reference to FIG. 9, upon further movement of actuator 140 toward the actuated position, e.g., upon further movement of shaft 12c toward shafts 12a and 12b, actuator 140 urges trough 265 of resiliently flexible body 264 of knife assembly 260 and, thus, knife blade 261, against the bias of resiliently flexible body 264, from the initial position to an extended position such that knife blade 261 is translated upwardly through blade channel 237 of tissue sealing plate 229. As knife blade 261 is translated upwardly through blade channel 237 of tissue sealing plate 229, cutting edge 266 of knife blade 261 is advanced through tissue grasped between jaw members 110, 120 to divide tissue. Actuator 140 may be configured to urge knife blade 261 from jaw member 120, completely through tissue grasped between jaw members 110, 120, and into blade channels 235, 218 of tissue sealing plate 219 and insulator 215, respectively, of jaw member 110, to help ensure that tissue grasped between jaw members 110, 120 has been completely divided. Thereafter, upon return of third shaft 12c to the first position, actuator 140 is returned to the un-actuated position within actuator slot 142 of jaw frame 122 such that knife blade 261 is returned to the initial position within jaw housing 221 of jaw members 120 under the bias of resiliently flexible body 264 of knife assembly 260. Jaw members 110, 120 may then be returned to the spaced-apart position to release the sealed and divided tissue and forceps 10 may be removed from the surgical site.

At the completion of the surgical procedure, disposable components 210, 220 may be removed from jaw frames 112, 122 of jaw members 110, 120, respectively, and discarded. Forceps 10 may then be sterilized and loaded with new disposable components 210, 220 for subsequent use.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
    first and second shaft members having respective first and second jaw members disposed at respective distal ends thereof, at least one of the first and second jaw members moveable relative to the other between a spaced-apart position and an approximated position for grasping tissue therebetween, the first jaw member including:
    a first jaw frame fixedly engaged to the first shaft member; and
    a disposable assembly releasably engageable with the first jaw frame, the disposable assembly including:
    a first disposable jaw housing;
    a first seal plate engaged to the first disposable jaw housing and including a longitudinally-extending blade channel defined at least partially therethrough;
    a resiliently flexible member defining a V-shaped configuration including first and second free ends and a trough, the first and second free ends supported within the first disposable jaw housing; and
    a knife engaged to the trough of the resiliently flexible member and biased toward an initial position, wherein the knife is disposed within the first disposable jaw housing, the knife moveable relative to the first disposable jaw housing between the initial position and an extended position upon flexion of the resiliently flexible member, wherein, in the extended position, the knife extends at least partially from the first disposable jaw housing through the longitudinally-extending blade channel of the first seal plate towards the second jaw member to cut tissue grasped between the first and second jaw members.

2. The forceps according to claim 1, further comprising an actuator disposed within the first jaw frame, the actuator selectively moveable from an un-actuated position to an actuated position to move the knife from the initial position to the extended position.

3. The forceps according to claim 2, further comprising a third shaft member, the third shaft member coupled to the actuator and extending proximally therefrom, the third shaft member moveable between a first position and a second position to move the actuator between the un-actuated position and the actuated position.

4. The forceps according to claim 1, wherein the first seal plate is adapted to connect to a source of electrosurgical energy for conducting energy through tissue grasped between the first and second jaw members.

5. The forceps according to claim 1, wherein the second jaw member includes:
   a second jaw frame fixedly engaged to the second shaft member; and
   a second disposable assembly releasably engageable with the second jaw frame.

6. The forceps according to claim 5, wherein the second disposable assembly includes a second disposable jaw housing and a second seal plate engaged to the second disposable jaw housing.

7. The forceps according to claim 6, wherein the second seal plate includes a longitudinally-extending blade channel defined at least partially therethrough, the blade channel configured for passage of the knife therethrough upon movement of the knife to the extended position.

8. The forceps according to claim 1, wherein the first disposable jaw housing includes at least one engagement feature configured to releasably engage a complementary engagement feature defined within the first jaw frame.

\* \* \* \* \*